United States Patent [19]

Audousset et al.

[11] Patent Number: 5,518,507
[45] Date of Patent: May 21, 1996

[54] COMPOSITION FOR THE OXIDATION DYEING OF KERATINOUS FIBRES, COMPRISING A PARA-PHENYLENEDIAMINE DERIVATIVE AND META-PHENYLENEDIAMINE DERIVATIVE, AND DYEING PROCESS USING SUCH A COMPOSITION

[75] Inventors: Marie-Pascale Audousset, Asnieres; Jean Cotteret, Verneuil S/Seine, both of France

[73] Assignee: L'Oreal, Paris, France

[21] Appl. No.: 361,669

[22] Filed: Dec. 22, 1994

[30]  Foreign Application Priority Data

Jan. 24, 1994 [FR] France .................................. 94 00700

[51] Int. Cl.⁶ ..................................................... A61K 7/13
[52] U.S. Cl. .......................... 8/411; 8/406; 8/408; 8/410; 8/416
[58] Field of Search ............................... 8/405, 406, 408, 8/411, 410, 416

[56]  References Cited

U.S. PATENT DOCUMENTS

| | | | |
|---|---|---|---|
| 4,125,367 | 11/1978 | Bugaut et al. | 8/411 |
| 4,840,639 | 6/1989 | Husemeyer et al. | 8/410 |
| 4,854,935 | 8/1989 | Clausen et al. | 8/411 |
| 4,904,275 | 2/1990 | Grollier | 8/411 |
| 5,224,965 | 7/1993 | Clausen et al. | 8/411 |
| 5,344,464 | 9/1994 | Madrange et al. | 8/411 |

FOREIGN PATENT DOCUMENTS

| | | |
|---|---|---|
| 0007537 | 2/1980 | European Pat. Off. . |
| 0252351 | 1/1988 | European Pat. Off. . |
| 1597034 | 9/1981 | United Kingdom . |
| 2085483 | 4/1982 | United Kingdom . |

*Primary Examiner*—Paul Lieberman
*Assistant Examiner*—Caroline L. Dusheck
*Attorney, Agent, or Firm*—Finnegan, Henderson, Farabow, Garrett and Dunner

[57]  ABSTRACT

A composition for the oxidation dyeing of keratinous fibres, in particular human keratinous fibres such as hair, of the type comprising, in a medium suitable for dyeing, the medium containing at least one para-phenylenediamine oxidation dye precursor which is substituted in the 2 position on the benzene ring or an acid addition salt thereof, and at least one specific meta-phenylenediamine coupling agent or an acid addition salt thereof. The use of this composition for dyeing keratinous fibres, in particular human keratinous fibres such as hair.

22 Claims, No Drawings

COMPOSITION FOR THE OXIDATION DYEING OF KERATINOUS FIBRES, COMPRISING A PARA-PHENYLENEDIAMINE DERIVATIVE AND META-PHENYLENEDIAMINE DERIVATIVE, AND DYEING PROCESS USING SUCH A COMPOSITION

The present invention is directed to a composition for the oxidation dyeing of keratinous fibres, in particular human keratinous fibres such as hair, which composition comprises, in combination, at least one para-phenylenediamine which is substituted in the 2 position on the benzene ring, and at least one meta-phenylenediamine, the structures of which are provided in the description below. The present invention is also directed to the use of such a composition.

It is known to dye keratinous fibres, in particular human keratinous fibres such as hair, with dyeing compositions containing oxidation dye precursors, in particular ortho- or para-phenylenediamines. ortho- or para-aminophenols, which are generally referred to as "oxidation bases," and coupling agents, which are also referred to as coloration modifiers, more particularly meta-phenylenediamines, meta-aminophenols and meta-diphenols. These compositions enable the "background" colorations, obtained with the products of the condensation of the oxidation bases, to be modified and to be enriched with glints.

In the field of oxidation dyeing of keratinous fibres, in particular human keratinous fibres such as hair, oxidation dye precursors and coupling agents which are capable of generating, when they are combined, a blue coloration which has satisfactory resistance to light, to washing, to inclement weather, to perspiration and to the various treatments to which hair may be subjected, are actively sought. Hitherto, these colorations were obtained with dyes based on para-phenylenediamine. However, the use of para-phenylenediamine is currently being questioned for toxicological reasons.

After considerable research conducted in this direction, it has been discovered that it is possible to obtain new non-toxic dyes which generate colorations ranging from blue to blue-purple and which are both intense and resistant, by combining a para-phenylenediamine which is substituted in the 2 position on the benzene ring with a meta-phenylenediamine, which compounds have the structures which are respectively, defined below. This discovery forms the basis of the present invention.

The present invention is thus directed to a composition for the oxidation dyeing of keratinous fibres, in particular human keratinous fibres such as hair, comprising a medium suitable for dyeing, the medium containing at least one para-phenylenediamine oxidation dye precursor of formula (I):

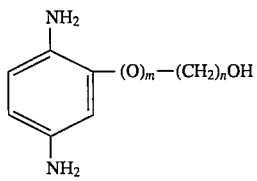

in which m is an integer equal to zero or 1; and n is an integer ranging from 1 to 4 inclusively; and/or at least one acid addition salt thereof; and at least one meta-phenylenediamine coupling agent of formula (II):

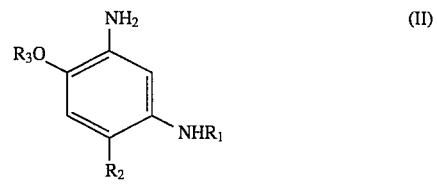

in which $R_1$ represents a hydrogen atom, an alkyl radical containing from 1 to 3 carbon atoms or a monohydroxyalkyl radical containing from 2 to 3 carbon atoms; $R_2$ represents a hydrogen atoms, a mono- or polyhydroxyalkoxy radical containing from 2 to 3 carbon atoms and further containing 1 to 2 hydroxyl groups; $R_3$ represents an alkyl radical containing from 1 to 3 carbon atoms, a mono- or polyhydroxyalkyl radical containing from 2 to 3 carbon atoms and further containing 1 to 2 hydroxyl groups, an aminoalkyl radical containing from 2 to 3 carbon atoms, or a 2,4-diaminophenoxyalkyl group in which the alkyl radical contains from 1 to 4 carbon atoms,and/or at least one acid addition salt thereof; with the proviso that when $R_1$ represents a hydrogen atom or an alkyl radical, $R_3$ is other than an alkyl radical, and, when $R_2$ represents a mono- or polyhydroxyalkoxy radical, $R_1$ necessarily represents a hydrogen atom and $R_3$ represents a mono- or polyhydroxyalkyl radical.

The present invention is also directed to a ready-to-use composition containing at least the composition for oxidation dyeing described above and optionally the various other agents used for dyeing keratinous fibres, in particular human keratinous fibres such as hair, defined above and also containing an oxidizing agent. A ready to use composition according to the invention preferably has a pH ranging from 3 to 11.

The present invention also contemplates a process for dyeing keratinous fibres, in particular human keratinous fibres such as hair, which comprises the steps of: applying to the fibres at least one dyeing composition of the present invention and using an oxidizing agent, the oxidizing agent being applied to the fibres simultaneously with or subsequent to the dyeing composition, to develop the colour of the dyeing composition in an acidic, neutral or alkaline medium.

The present invention further contemplates a kit, or device, for dyeing keratinous fibres, in particular human keratinous fibres such as hair, which comprises at least two compartments, one of the compartments containing at least one para-phenylenediamine oxidation dye precursor of formula (I), and at least one meta-phenylenediamine coupling agent of formula (II), and another of the compartments containing a composition (B) containing an oxidizing agent in a medium suitable for dyeing.

A further embodiment of the present invention includes a process for dyeing keratinous fibres, in particular human keratinous fibres such as hair, comprising the steps of: applying to the fibres a dyeing composition in accordance with the present invention, the dyeing composition being obtained from a kit for dyeing keratinous fibres, in particular human keratinous fibres such as hair, which kit comprises at least two compartments, one of the compartments containing the dyeing composition in accordance with the present invention, and another of the compartments containing a dyeing composition (B) containing an oxidizing agent in a medium suitable for dyeing; and using the oxidizing agent and the suitable dyeing medium, the agent and medium being applied to the fibres simultaneously with or subsequent to the dyeing composition, to develop the colour of the dyeing composition in the medium.

The composition and process of the present invention are used for the dyeing of keratinous fibres in general. The preferred form of keratinous fibres taught by the present invention is human keratinous fibres.

The new dyes obtained in accordance with the present invention make it possible to achieve colorations ranging from blue to blue-purple, which colorations are sustained, nontoxic and particularly resistant at the same time to light, to washing, to inclement weather, to perspiration and to the various treatments to which hair may be subjected. Most particularly, the colorations achieved by the present invention are very resistant to shampoos. Other characteristics, aspects, aims and advantages of the present invention will emerge more clearly upon reading the description and the examples which follow.

The acid salts which may be used according to the invention are preferably independently chosen from hydrochlorides, sulphates, hydrobromides and tartrates.

Among the oxidation dye precursors of formula (I) which may be used within the context of the present invention, the following compounds are preferably used: 2-(β-hydroxymethyl)-paraphenylenediamine, 2-(β-hydroxyethyl)-paraphenylenediamine and 2-(β-hydroxyethyloxy)-para-phenylenediamine. The concentration of oxidation dye precursor(s) of formula (I) or of acid addition salts thereof may preferably range from approximately 0.01% to 10% by weight relative to the total weight of the dye composition, and more preferably range from approximately 0.05% to 5% by weight.

Among the coupling agents of formula (II), the following compounds are preferably used: 1-(β-hydroxy-ethyloxy)-2, 4-diaminobenzene, 1,3-bis(2,4-diaminophenoxy)propane, 1,3-bis(2,4-diaminophenoxy)methane, 1-methoxy-2-amino-4-(β-hydroxyethylamino)benzene, 1-(β-aminoethyloxy)-2, 4-diaminobenzene, 1-(β-hydroxyethyloxy)-2-amino-4-methylaminobenzene, 1,3-diamino-4,6-bis(β-hydroxyethyloxy)benzene and 1-(β,γ-dihydroxypropyloxy)-2,4-diaminobenzene. The concentration of coupling agent(s) of formula (II) or of acid addition salts thereof may preferably range from approximately 0.001% to 3% by weight relative to the total weight of the dye composition, and more preferably range from approximately 0.05% to 2% by weight.

Oxidation dye compositions which are more preferred according to the invention comprise, as an oxidation dye precursor, 2-(β-hydroxyethyl)-para-phenylenediamine or an acid addition salt thereof and, as a coupling agent, 1-(β-hydroxyethyloxy)-2,4-diaminobenzene or 1-methoxy-2-amino-4-(β-hydroxyethylamino)benzene or an acid addition salt of either compound. Other dye compositions, which are also preferably used, comprise, as an oxidation dye precursor, 2-(β-hydroxyethyloxy)-para-phenylenediamine or an acid addition salt thereof and, as a coupling agent, 1-(β-hydroxyethyloxy)-2,4-diaminobenzene or 1-methoxy-2-amino-4-(β -hydroxyethylamino)benzene or an acid addition salt thereof.

The oxidizing agent is preferably chosen from hydrogen peroxide, urea peroxide, alkali metal bromates and persalts such as perborates and persulphates. It is more preferable to use hydrogen peroxide as the oxidizing agent.

Composition (A), which contains the combination of the dyes as described above, may have a pH which preferably ranges from 3 to 11. The pH may be adjusted to the desired value either by using basifying agents which are conventionally used for dyeing keratinous fibres, such as aqueous ammonia, alkali metal carbonates, alkanolamines such as, for example, mono-, di- and triethanolamines and the derivatives thereof, sodium hydroxide or potassium hydroxide, or the compounds of formula:

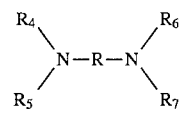

is which R is a propylene residue which is optionally substituted with a hydroxyl group or a $C_1$–$C_4$ alkyl radical; $R_4$, $R_5$, $R_6$ and $R_7$ each may independently represent a hydrogen atom, a $C_1$–$C_4$ alkyl radical or a $C_1$–$C_4$ hydroxyalkyl radical; or by using standard acidifying agents, such as inorganic or organic acids, for example, hydrochloric acid, tartaric acid, citric acid and phosphoric acid.

The pH of the composition (B) containing the oxidizing agent as described above, is such that, after mixing with the composition (A), the pH of the composition applied to the keratinous fibres, in particular human keratinous fibres, preferably ranges from 3 to 11. The pH can be adjusted to the desired value using acidifying agents, or possibly basifying agents, which are well-known to those skilled in the art, such as those described above. The oxidizing composition (B) preferably comprises a solution of hydrogen peroxide.

According to a preferred embodiment of the dyeing process of the invention, the dyeing composition (A) described above is mixed, at the time of use, with an oxidizing solution in an amount sufficient to develop a coloration. The mixture obtained is then applied to keratinous fibres, preferably human keratinous fibres, and is left to stand for preferably 5 to 40 minutes, and more preferably for 15 to 30 minutes, after which the fibres are rinsed, washed with shampoo, rinsed again and dried.

In addition to the dyes discussed above, the dyeing compositions of the present invention may also contain other direct dyes and/or coupling agents, particularly in order to modify the shades or to enrich the shades with glints.

The dyeing compositions of the present invention may also contain antioxidants. Preferred antioxidants include sodium sulphite, thioglycolic acid, thiolactic acid, sodium bisulphite, dehydroascorbic acid, hydroquinone, 2-methylhydroquinone, tertbutylhydroquinone and homogentisic acid, and are generally present in proportions preferably ranging from approximately 0.05% to 1.5% by weight relative to the total weight of the composition.

In another preferred embodiment, the dyeing compositions may also contain surface-active agents which are well-known in the art. The surface active agents may be present in proportions preferably ranging from approximately 0.5% to 55% by weight, and more preferably from 2% to 50% by weight, relative to the total weight of the composition. The dyeing compositions may also preferably contain organic solvents in proportions preferably ranging from approximately 1% to 40% by weight, and more preferably ranging from 5% to 30% by weight, relative to the total weight of the composition. The dyeing compositions may additionally contain any other adjuvant which is cosmetically acceptable and is known in the art related to the oxidation dyeing of hair.

The dyeing composition which is applied to the hair may preferably be provided in various forms, such as in the form of a liquid, a cream, a gel or any other form which is suitable for dyeing keratinous fibres, in particular human keratinous fibres such as hair. The dyeing composition may preferably be packaged under pressure in an aerosol can in the presence of a propellant and may be capable of forming a foam.

Concrete examples illustrating the invention will now be provided. To begin with, a definition will be provided of the tests used to evaluate the performance of the oxidation dyes according to the invention with regard to their resistance to perspiration, to light, to shampoos, to inclement weather and to permanent-waving.

Resistance To Perspiration:

A synthetic sweat solution of the following composition was used: 10 g of NaCl, 1 g of potassium hydrogen phosphate, 0.25 g of histidine, lactic acid to give pH=3.2 and distilled water to make up to 100 g. The locks of dyed hair were immersed in the sweat solution which was contained in a crystallizing dish covered with a watch glass, and were left for a period of 20 to 50 hours at 37° C. The locks were then rinsed and dried.

Resistance To Light (Xenotest):

The dyed hair was attached to a support (cardboard or plastic). These supports were arranged on sample holders which rotated around a xenon lamp for a duration which ranged from 20 to 80 hours, at a moisture content which ranged from 25 to 75% RH (Relative Humidity) and at a temperature of 25° C.

Resistance To Shampoos (Ahiba-Texomat Machine):

Locks of dyed hair were placed in a basket which was immersed in a solution of a standard shampoo. The basket was subjected to an up-and-down movement of variable frequency and to a rotational movement, which reproduced the action of manual rubbing, thereby causing the formation of foam.

After being treated for 3 minutes, the locks were removed and then rinsed and dried. They dyed locks may have been subjected to several consecutive shampoo tests.

Resistance To Inclement Weather (Combined Test):

-The dyed locks were exposed to strong light (Xenotest 40h), at a relative humidity of 60%, and simultaneously, every 12 hours and for a duration of 20 minutes, they were sprayed with water.

Resistance To Permanent-Waving:

The dyed locks were immersed in a Dulcia Vital permanent-wave reducing solution (L'Oréal), of strength which ranged from 1 to 3, for a duration which ranged from 10 to 20 minutes; the locks were rinsed; the locks were then soaked in a fixing (oxidizing) solution for 5 minutes. After being rinsed with water, washed with standard shampoo and being rinsed with water again, the locks were dried.

EXAMPLE 1

The following dye composition, in accordance with the invention, was prepared:

| | |
|---|---|
| 2-(β-Hydroxyethyl)-para-phenylenediamine dihydrochloride | 0.675 g |
| 1-(β-Hydroxyethyloxy)-2,4-diaminobenzene | 0.672 g |
| Polyglycerolated oleyl alcohol containing 2 mol of glycerol | 4.0 g |
| Polyglycerolated oleyl alcohol containing 4 mol of glycerol (78% of AM) | 5.7 g AM |
| Oleic acid | 3.0 g |
| Oleyl amine containing 2 mol of ethylene oxide, sold under the name Ethomeen 012 by the company AKZO | 7.0 g |
| Diethylaminopropyl laurylaminosuccinamate sodium salt containing 55% of AM | 3.0 g AM |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqueous solution containing 35% of AM | 0.4 g AM |
| Ammonium acetate | 0.8 g |
| Antioxidant, sequestering agent | qs |
| Fragrance, preserving agent | qs |
| Aqueous ammonia containing 20% of NH$_3$ | 10.0 g |
| Demineralized water qs | 100.0 g |

At the time of use, this composition was mixed weight-for-weight with 20 volumes of hydrogen peroxide (6% by weight), which had a pH of 3. A mixture having a pH of 9.8 was obtained. This mixture was then applied to grey hair containing 90% white hairs, for 30 minutes. After being rinsed, washed with shampoo, rinsed again and dried, the inventors believe the hair would be dyed a strong blue shade which would particularly resist shampoos remarkably well.

EXAMPLE 2

The following dye composition, in accordance with the invention, was prepared:

| | |
|---|---|
| 2-(β-hydroxyethyloxy)-para-phenylenediamine dihydrochloride | 0.723 g |
| 1-methoxy-2-amino-4-(β-hydroxyethylamino)-benzene | 0.759 g |
| Polyglycerolated oleyl alcohol containing 2 mol of glycerol | 4.0 g |
| Polyglycerolated oleyl alcohol containing 4 mol of glycerol (78% of AM) | 5.7 g AM |
| Oleic acid | 3.0 g |
| Oleyl amine containing 2 mol of ethylene oxide, sold under the name Ethomeen 012 by the company AKZO | 7.0 g |
| Diethylaminopropyl laurylaminosuccinamate sodium salt containing 55% of AM | 3.0 g AM |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqueous solution containing 35% of AM | 0.4 g AM |
| Ammonium acetate | 0.8 g |
| Antioxidant, sequestering agent | qs |
| Fragrance, preserving agent | qs |
| Aqueous ammonia containing 204 of NH$_3$ | 10.0 g |
| Demineralized water qs | 100.0 g |

At the time of use, this composition was mixed weight-for-weight with 20 volumes of hydrogen peroxide (6% by weight), which had a pH of 3. A mixture having a pH of 9.8 was obtained. This mixture was then applied to grey hair containing 90% white hairs, for 30 minutes. After being rinsed, washed with shampoo, rinsed again and dried, the inventors believe the hair would be dyed a strong blue shade which would particularly resist shampoos remarkably well.

What is claimed is:

1. A composition for the oxidation dyeing of keratinous fibres, comprising a medium suitable for dyeing, said medium containing at least one para-phenylenediamine oxidation dye precursor selected from a compound of formula (I):

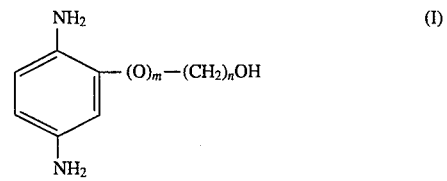

in which m is an integer equal to zero or 1, and n is an integer ranging from 1 to 4 inclusively, and an acid addition salt of the compound of formula (I);

and at least one meta-phenylenediamine coupling agent selected from a compound of formula (II):

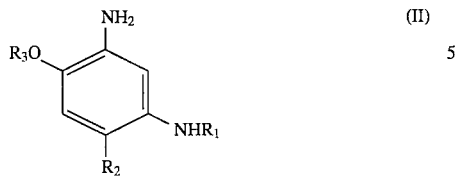

in which

R$_1$ represents a hydrogen atom, an alkyl radical containing from 1 to 3 carbon atoms or a monohydroxyalkyl radical containing from 2 to 3 carbon atoms;

R$_2$ represents a hydrogen atom, a mono- or polyhydroxyalkyl radical containing from 2 to 3 carbon atoms and containing 1 to 2 hydroxyl groups;

R$_3$ represents an alkyl radical containing from 1 to 3 carbon atoms, a mono- or polyhydroxyalkyl radical containing from 2 to 3 carbon atoms and containing 1 to 2 hydroxyl groups, an aminoalkyl radical containing from 2 to 3 carbon atoms, or a 2,4-diaminophenoxyalkyl group in which the alkyl radical contains from 1 to 4 carbon atoms and an acid addition salt of the compound of formula (II);

wherein said at least one para-phenylenediamine oxidation dye precursor and said at least one meta-phenylenediamine coupling agent are present in amounts effective to react with an oxidation agent to dye said keratinous fibres;

with the proviso that, when R$_1$ represents a hydrogen atom or an alkyl radical, R$_3$ is other than an alkyl radical, and, when R$_2$ represents a mono- or polyhydroxyalkoxy radical, R$_1$ necessarily represents a hydrogen atom and R$_3$ represents a mono- or polyhydroxyalkyl radical.

2. A dyeing composition according to claim 1, wherein said para-phenylenediamine oxidation dye precursor of formula (I) is selected from 2-(β-hydroxymethyl)-para-phenylenediamine, 2-(β-hydroxyethyl)-para-phenylenediamine, 2-(β-hydroxyethyloxy)-para-phenylenediamine and the acid addition salts thereof.

3. A dyeing composition according to claim 1, wherein said meta-phenylenediamine coupling agent of formula (II) is selected from 1-(β-hydroxyethyloxy)-2,4-diamino-benzene, 1,3-bis(2,4-diaminophenoxy)propane, 1,3-bis(2,4-diaminophenoxy)methane, 1-methoxy-2-amino-4-(β-hydroxyethylamino)benzene, 1-(β-aminoethyloxy)-2,4-diaminobenzene, 1-(β-hydroxyethyloxy)-2-amino-4-methylaminobenzene, 1,3-diamino-4,6-bis(β-hydroxyethyloxy)benzene, 1-(β,γ-dihydroxypropyloxy)-2,4-diaminobenzene and the acid addition salts thereof.

4. A dyeing composition according to claim 1, which comprises, as an oxidation dye precursor of formula (I), at least 2-(β-hydroxyethyl)-para-phenylenediamine or an acid addition salt thereof and, as a coupling agent, at least 1-(β-hydroxyethyloxy)-2,4-diaminobenzene or an acid addition salt thereof or 1-methoxy-2-amino-4-(β-hydroxyethylamino)benzene or an acid addition salt thereof.

5. A dyeing composition according to claim 1, which comprises, as an oxidation dye precursor of formula (I), at least 2-(β-hydroxyethyloxy)-paraphenylenediamine or an acid addition salt thereof and, as a coupling agent, at least 1-(β-hydroxyethyloxy)-2,4-diaminobenzene or 1-methoxy-2-amino-4-(β-hydroxyethylamino)benzene or an acid addition salt thereof.

6. A dyeing composition according to claim 1, wherein said acid addition salt of said dye precursor and said acid addition salt of said coupling agent are independently selected from hydrochlorides, sulphates, hydrobromides and tartrates.

7. A dyeing composition according to claim 1, wherein said para-phenylenediamine oxidation dye precursor of formula (I), or an acid addition salt thereof, is present in a concentration ranging from 0.01% to 10% by weight, relative to the total weight of the composition, and the coupling agent of formula (II), or an acid addition salt thereof, is present in a concentration ranging from 0.001% to 3% by weight relative to the total weight of the composition.

8. A dyeing composition according to claim 7, wherein said para-phenylenediamine oxidation dye precursor of formula (I), or an acid addition salt thereof, is present in a concentration ranging from 0.05% to 5% by weight, relative to the total weight of the composition, and the meta-phenylenediamine coupling agent of formula (II), or an acid addition salt thereof, is present in a concentration ranging from 0.05% to 2% by weight relative to the total weight of the composition.

9. A dyeing composition according to claim 1, which is a ready-to-use composition, and which further comprises an oxidizing agent and has a pH ranging from 3 to 11.

10. A dyeing composition according to claim 1, wherein said keratinous fibres are human keratinous fibres.

11. A process for dyeing keratinous fibres, comprising the steps of:

(i) applying to said fibres the dyeing composition according to claim 1; and (ii) developing the colour of said dyeing composition in an acidic, neutral or alkaline medium by applying an oxidizing agent to said fibres simultaneously with or subsequently to said dyeing composition.

12. A process according to claim 11, wherein said oxidizing agent is added to said dyeing composition at the time of applying in said step (i).

13. A process according to claim 11, wherein said oxidizing agent is separately contained in a composition (B) and is separately applied to said fibres simultaneously with said dyeing composition.

14. A process according to claim 11, where said oxidizing agent is separately contained in a composition (B) and separately applied to said fibres subsequent to said application of said dyeing composition.

15. A process according to claim 11, wherein said keratinous fibres are human keratinous fibres.

16. A kit for dyeing keratinous fibres comprising at least two compartments, one of said compartments containing a dyeing composition according to claim 1, and another of said compartments containing a composition (B) containing an oxidizing agent in a medium suitable for dyeing.

17. A kit according to claim 16, wherein said keratinous fibres are human keratinous fibres.

18. A process for dyeing keratinous fibres comprising the steps of:

(i) applying to said fibres a dyeing composition according to claim 1, said dyeing composition being obtained from a kit for dyeing keratinous fibres comprising at least two compartments, one of said compartments containing said dyeing composition according to claim 1 and another of said compartments containing a composition (B) containing an oxidizing agent in a medium suitable for dyeing; and (ii) developing the colour of said dyeing composition in an acidic, neutral or alkaline medium by applying an oxidizing agent to said fibres simultaneously with or subsequent to said dyeing composition.

19. A process according to claim 18, wherein said oxidizing agent is applied to said fibres simultaneously with said dyeing composition.

20. A process according to claim 18, wherein said oxidizing agent is applied to said fibres subsequent to said dyeing composition.

21. A process according to claim 18, wherein said keratinous fibres are human keratinous fibres.

22. A dyeing composition according to claim 1, wherein $R_3$ represents a mono- or polyhydroxyalkyl radical containing from 2 to 3 carbon atoms and containing 1 to 2 hydroxyl groups.

* * * * *